US008906968B2

(12) United States Patent
Di Maiuta et al.

(10) Patent No.: US 8,906,968 B2
(45) Date of Patent: Dec. 9, 2014

(54) PROCESS FOR BACTERIAL STABILIZING OF AQUEOUS GROUND NATURAL CALCIUM CARBONATE AND/OR PRECIPITATED CALCIUM CARBONATE AND/OR DOLOMITE AND/OR SURFACE-REACTED CALCIUM CARBONATE-COMPRISING MINERAL PREPARATIONS

(75) Inventors: Nicola Di Maiuta, Zuchwil (CH); Patrick Schwarzentruber, Habsburg (CH)

(73) Assignee: Omya International AG, Oftringen (CH)

( * ) Notice: Subject to any disclaimer, the term of this patent is extended or adjusted under 35 U.S.C. 154(b) by 130 days.

(21) Appl. No.: 13/511,549

(22) PCT Filed: Dec. 6, 2010

(86) PCT No.: PCT/EP2010/068966
§ 371 (c)(1),
(2), (4) Date: May 23, 2012

(87) PCT Pub. No.: WO2011/069961
PCT Pub. Date: Jun. 16, 2011

(65) Prior Publication Data
US 2012/0277322 A1    Nov. 1, 2012

Related U.S. Application Data

(60) Provisional application No. 61/284,199, filed on Dec. 14, 2009.

(30) Foreign Application Priority Data

Dec. 7, 2009  (EP) ..................................... 09178228
Jun. 11, 2010 (EP) ..................................... 10165674

(51) Int. Cl.
*A01N 25/00* (2006.01)
*A61K 47/00* (2006.01)
*A61K 9/00* (2006.01)
*A01N 33/08* (2006.01)
*A01N 43/80* (2006.01)

(52) U.S. Cl.
CPC ............... *A01N 33/08* (2013.01); *A01N 43/80* (2013.01)
USPC ......................................... 514/770; 424/400

(58) Field of Classification Search
None
See application file for complete search history.

(56) References Cited

U.S. PATENT DOCUMENTS

| 4,345,945 A | 8/1982 | Robinson |
| 4,370,171 A | 1/1983 | Robinson et al. |
| 4,655,815 A | 4/1987 | Jakubowski |
| 5,278,178 A | 1/1994 | Hsu |
| 5,278,248 A | 1/1994 | Egraz et al. |
| 5,496,398 A | 3/1996 | Drew et al. |
| 2001/0009682 A1 | 7/2001 | Whiteley |
| 2006/0111410 A1 | 5/2006 | Wachtler et al. |
| 2011/0097311 A1 | 4/2011 | Di Maiuta et al. |

FOREIGN PATENT DOCUMENTS

| CZ | 240507 B1 | 2/1986 | |
| EP | 1362897 A2 | 11/2003 | |
| EP | 1661587 A1 | 5/2006 | |
| EP | 2108260 A2 | 10/2009 | |
| JP | 8012505 A | 1/1996 | |
| JP | 11012109 A | 1/1999 | |
| JP | 4088664 B2 * | 5/2008 | ............. A01N 43/78 |
| WO | 0036913 A2 | 6/2000 | |
| WO | 0039222 A1 | 7/2000 | |
| WO | 02052941 A1 | 7/2002 | |
| WO | 2004040979 A1 | 5/2004 | |
| WO | 2004083316 A1 | 9/2004 | |
| WO | 2005055720 A1 | 6/2005 | |
| WO | 2005121257 A1 | 12/2005 | |
| WO | 2006016991 A1 | 2/2006 | |
| WO | 2006057993 A1 | 6/2006 | |
| WO | 2006074788 A2 | 7/2006 | |
| WO | 2006079911 A1 | 8/2006 | |
| WO | 2008088632 A2 | 7/2008 | |
| WO | WO 2008088632 A2 * | 7/2008 | ............. A01N 33/08 |
| WO | 2009074492 A1 | 6/2009 | |

OTHER PUBLICATIONS

English machine translation dated Feb. 15, 2013 of Matsumoto et al., JP 4088664 B2; published May 21, 2008.*
Sandin et al., "Selective Toxicity of Alkanolamines", Mar. 1990, Antimicrobial Agents and Chemotherapy, vol. 34, No. 3, pp. 491-493.*
The International Search Report, dated Feb. 15, 2011 for PCT Application No. PCT/EP2010/068966.
The Written Opinion of the International Searching Authority, dated Feb. 15, 2011 for PCT Application No. PCT/EP2010/068966.
Bennett et al. "Antimicrobial Properties of Butanolamines and Propanolamines in Metal Working Fluids." J. Gen. Appl. Microbiol., 25, 63-69 (1979).
Communication dated Oct. 7, 2013 for related European Application No. EP 10 787 753.2.
Sandin et al. "Selective Toxicity of Alkanolamines." Antimicrobial Agents and Chemotherapy, Mar. 1990, pp. 491-493.

* cited by examiner

*Primary Examiner* — Michael B Pallay
(74) *Attorney, Agent, or Firm* — Amster, Rothstein & Ebenstein LLP

(57) ABSTRACT

This invention discloses a process for stabilizing an aqueous mineral preparation comprising a step of adding at least one aldehyde-containing and/or aldehyde-releasing and/or phenolic and/or isothiazoline biocide to said aqueous mineral preparation.

34 Claims, No Drawings

PROCESS FOR BACTERIAL STABILIZING OF AQUEOUS GROUND NATURAL CALCIUM CARBONATE AND/OR PRECIPITATED CALCIUM CARBONATE AND/OR DOLOMITE AND/OR SURFACE-REACTED CALCIUM CARBONATE-COMPRISING MINERAL PREPARATIONS

CROSS-REFERENCE TO RELATED APPLICATIONS

This application is a U.S. National phase of PCT Application No. PCT/EP2010/068966, filed Dec. 6, 2010, which claims priority to European Application No. 09178228.4, filed Dec. 7, 2009, U.S. Provisional Application No. 61/284, 199, filed Dec. 14, 2009 and European Application No. EP 10165674.2, filed Jun. 11, 2010.

The invention relates to a process for bacterial stabilizing of aqueous ground natural calcium carbonate and/or precipitated calcium carbonate and/or dolomite and/or surface-reacted calcium carbonate-comprising mineral preparations and to the use of biocidal activity enhancing compounds.

In practice, aqueous preparations and especially suspensions or dispersions of water-insoluble mineral solids are used extensively in the paper, paint, rubber and plastics industries as coatings, fillers, extenders and pigments for papermaking as well as aqueous lacquers and paints. For example, suspensions or dispersions of mineral solids are used in the paper industry in large amounts as filler and/or as a component in the preparation of coated paper. Typical aqueous preparations of water-insoluble solids are characterized in that they comprise water, a water-insoluble solid compound and optionally further additives, such as dispersing agents, in the form of a suspension or dispersion. Water-soluble polymers and copolymers which may be used as e.g. dispersant and/or grinding aid in such preparation are, for example, described in U.S. Pat. No. 5,278,248.

The aforementioned aqueous preparations are often subject to contamination by microorganisms such as aerobic and anaerobic bacteria resulting in changes in the preparation properties, such as discolorations or reductions in other quality parameters, which negatively affect their commercial value. Therefore, the manufacturers of such aqueous preparations usually take measures for stabilizing the suspensions, dispersions or slurries. For example, it is known that aldehyde-releasing biocides reduce the growth and accumulation of such microorganisms in aqueous preparations and, thus, reduce the tendency of undesired alterations of these preparations, like unpleasant odours.

For ensuring an acceptable microbiological quality of aqueous preparations, biocides are used over the entire life cycle of the preparation (production, storage, transport, use). In the art, several approaches for improving the microbiological quality of aqueous preparations have been proposed. For example, EP 1 139 741 describes aqueous suspensions or dispersions of minerals, fillers and/or pigments, containing a microbicidal agent in the form of a solution and derivatives of phenol in partially neutralized form. U.S. Pat. No. 5,496,398 relates to a process for the reduction of microorganisms in kaolin clay slurries by a combination of low temperature heat and reduced levels of a microbiocidal agent. WO 02/052941 describes biocide compositions for incorporation into paints, coating, plasters and plastics comprising at least one metal oxide and at least one metal salt. US 2006/0111410 mentions a mixture comprising 1,2-benzisothiazolinone (BIT) and tetramethylolacetylenediurea (TMAD) for protecting industrial materials and products against attack and destruction by microorganisms. Furthermore, it is suggested in the art to add formaldehyde-releasing substances to such aqueous preparations for improving the microbiologically related quality. For example, U.S. Pat. No. 4,655,815 mentions an antimicrobial composition comprising a formaldehyde donor. Furthermore, WO 2006/079911 describes a method of protection against microorganisms by increasing the $OH^+$ ion concentration of the suspension.

WO 2004/040979 A1 relates to synergistic antimicrobial mixtures containing 1,2-benzisothiazolinone (BIT) and benzylhemiformal (BHF). The corresponding mixtures are used, for example, for suspensions of pigments.

EP 1 362 897 relates to the use of secondary or tertiary alkanolamine as biocide enhancer in paints, coatings, sealants and adhesives.

EP 1 661 587 A1 relates to germicidal compositions including phthalaldehyde as an active ingredient. It is indicated in EP 1 661 587 A1 that carbonate salts and bicarbonate salts may enhance the germicidal efficacy of phthalaldehydes.

US 2001/0009682 A1 relates to disinfectant concentrates having improved biocidal activity which may contain an aldehyde such as glutaraldehyde, a glycol and a lithium based buffer.

Finally, EP 2 108 260 refers to a process for bacterial stabilizing of an aqueous preparation, said preparation comprising at least one mineral and at least one strain of bacteria which is resistant to, tolerant to and/or degrade aldehyde-releasing and/or aldehyde-based biocides, wherein the process comprises the steps of: (a) adding to the aqueous preparation one or more aldehyde-releasing and/or aldehyde-based biocides in an amount such that the total amount of aldehyde-releasing and/or aldehyde-based biocides in the aqueous preparation is from 250 ppm to 5000 ppm, calculated relative to the water in the preparation; (b) adding at least one water soluble lithium compound to the aqueous preparation in an amount such that the total amount of solubilised lithium in the aqueous preparation is from 1000 to 3000 ppm, calculated relative to the weight of water in the preparation, where steps (a) and (b) may be carried out simultaneously, or separately in any order.

Because of the limited activity spectrum of several biocides, the efficacy of such biocides against bacteria is not always satisfactory and, thus, the obtained action is in some cases insufficient to avoid microbially induced alteration of aqueous preparations.

Thus, there is still a need for adequate compositions providing sufficient biocidal activity in aqueous preparations such as suspensions and dispersions of mineral materials comprising ground natural calcium carbonate in order to achieve a longer lasting and sufficient stabilization.

These and other objectives of the present invention can be solved by a process and a use as described in the present invention and defined in the claims.

One aspect of the present application resides in a process for stabilising an aqueous mineral preparation comprising a step of:
(a) adding at least one aldehyde-containing and/or aldehyde-releasing and/or phenolic and/or isothiazoline biocide to said aqueous mineral preparation;
characterised in that:
said mineral comprises at least one of: a ground natural calcium carbonate, a precipitated calcium carbonate, a dolomite, a surface-modified calcium carbonate, or a mixture thereof;

said process comprises a step (b), which may be simultaneous and/or distinct relative to step (a), of adding at least one monoalcohol primary alkanol amine to said aqueous mineral preparation;

said biocide(s) are added to said aqueous preparation in an amount corresponding to from 90 to 1350 ppm based on the weight of the aqueous phase of said aqueous preparation; and said monoalcohol primary alkanol amine(s) are added to said aqueous preparation in an amount corresponding to from 600 to 1200 ppm based on the weight of the aqueous phase of said aqueous preparation.

According to the present invention, the wording "stabilising an aqueous preparation" implies no "significant growth" of bacteria. Preferably, the stabilization leads to a reduction and/or maintenance of the Total Viable Count (TVC, given in colony forming unit per milliliter (cfu/ml), as measured according to the measurement method defined in the Examples section hereafter) of the treated aqueous preparation to a value of less than $10^4$ cfu/ml, more preferably to a value of less than $10^3$ cfu/ml, and even more preferably to a value of less than or equal to $10^2$ cfu/ml.

An "aqueous mineral preparation" in the meaning of the present invention is a suspension comprising ground natural calcium carbonate and/or precipitated calcium carbonate and/or dolomite and/or surface-reacted calcium carbonate-comprising minerals and water and optionally further additives. Preparations having the required solids content may be viscous and require the implementation of dispersing agents or other rheology modifying agents.

The solids content in the meaning of the present application corresponds to the residual weight of the aqueous preparation following evaporation of the aqueous phase and is determined according to the measurement method described in the Examples section herebelow.

The weight of the aqueous phase is determined by subtracting the residual weight of the aqueous preparation following evaporation of the aqueous phase (determined according to the measurement method described in the Examples section herebelow) from the total weight of the aqueous preparation.

In accordance with the present invention, an "aldehyde-releasing biocide" refers to a compound which is able to release mono-, di-, and/or tri-aldehyde.

In accordance with the present invention, an "aldehyde-based biocide" refers to a biocide which has one or more aldehyde-group.

In accordance with the present invention, a "phenolic biocide" refers to a biocide which comprises at least one phenol functional group.

In accordance with the present invention, an "isothiazoline biocide" refers to a biocide which comprises at least one isothiazoline group.

According to the present invention, a monoalcohol primary alkanol amine is an alkanol amine having only one alcohol functional group and in which the amine features only one non-hydrogen, alkyl substituent. Such alkanol amines may be generally represented by the chemical formula: HO—R—NH2, where R is an alkyl group that is linear or branched, optionally featuring non-hydrogen-based substituents.

Furthermore, the present invention refers to the use of at least one monoalcohol primary alkanol amine as a biocidal activity enhancing compound in an aqueous ground natural calcium carbonate and/or precipitated calcium carbonate and/or dolomite and/or surface-reacted calcium carbonate-comprising mineral preparation comprising at least one aldehyde-containing and/or aldehyde-releasing and/or phenolic and/or isothiazoline biocide, where the total amount of said biocide(s) in the aqueous preparation is from 90 ppm to 1350 ppm, calculated relative to the weight of the aqueous phase of said preparation, and the total amount of said monoalcohol primary alkanol amine(s) in the aqueous preparation is from 600 to 1200 ppm, calculated relative to the weight of the aqueous phase of said preparation.

Monoalcohol primary alkanol amines, such as 2-amino-2-methyl-1-propanol (AMP), are known additives employed in a variety of industries, including in mineral preparations.

From the webpage "www.dow.com/angus/prod/paint.htm", 2-amino-2-methyl-1-propanol is known to disperse calcium carbonate and other pigments. Technical Bulletin 67 issued by the Angus Chemical Company, states that AMP-95 (2-amino-2-methyl-1-propanol containing 5% water) "is widely recognised as a multi-functional additive for all types of latex emulsion paints. In formulation, AMP-95 can be used as a powerful co-dispersant to prevent the reagglomeration of pigments."

U.S. Pat. No. 4,370,171 discloses a method for dispersing a comminuted solid in aqueous medium using a combination of an alkanolamine and a polymeric carboxylic acid as dispersing agent, while U.S. Pat. No. 4,345,945 refers to the dispersing of a comminuted solid in aqueous medium using a combination of a salt of an alkanolamine and a phosphorous acid. WO 2006/057993 likewise refers to the use of salts and/or esters of alkanolamines, which may be AMP, and polyprotic acids as pigment dispersing agents.

Indeed, it is all the more to the credit of the present Applicant that despite the common use of monoalcohol primary alkanolamines, such as AMP, as dispersant, corrosion inhibitor, pH regulator, and other uses, it has never been recognised that monoalcohol primary alkanolamines might be appropriately dosed to serve as a biocidal activity enhancing compound in the environment of a selected aqueous mineral preparation comprising ground natural calcium carbonate and/or precipitated calcium carbonate and/or dolomite and/or surface-reacted calcium carbonate.

A biocidal activity enhancing compound referred to herein is a compound which is capable of increasing or inducing the biocidal activity of one or more biocides in comparison with a preparation having no such biocidal activity enhancing compound but, e.g. only one or more biocides in an amount such that the total amount of biocides in the aqueous preparation is from 90 to 1350 ppm, calculated relative to the water in the preparation.

Notably, the biocidal activity enhancing compound may be capable of inducing the biocidal activity of one or more biocides when these biocides are dosed in an amount that is less than their Minimum Inhibition Concentration (MIC), the MIC being defined as the lowest concentration needed to reduce the TVC to the order of $10^2$ cfu/ml.

When monoalcohol primary alkanolamines, such as AMP, are shown in combination with biocides, it is only in applications that are unrelated to the specific aqueous preparations of ground natural calcium carbonate and/or precipitated calcium carbonate and/or dolomite and/or surface-reacted calcium carbonate-comprising minerals of the present invention. Even in these cases, it is often shown to be necessary to add monoalcohol primary alkanolamines in combination with a biocide in amounts that are impracticable for the skilled man charged with identifying such additives for use in aqueous preparations of mineral materials.

WO 2006/016991 refers to a microorganism control combination, formed of a biocidal control agent and a specified alkylamine ethoxylate, which is a secondary or tertiary amine, for liquid hydrocarbon systems containing water. Targeted microorganisms are those present at the water-hydrocarbon interface. Table 1 of WO 2006/016991 shows that when applied to Trypticase Soy Broth (TSB)-based plates inoculated with *Pseudomonas aeruginosa*, more than 4000 ppm of AMP are needed in combination with 500 ppm of triazine biocide in order to significantly influence the growth rate of the bacteria.

The Applicant would, relative to this reference, further point out that surprisingly, monoalcohol tertiary alkanolamines do not provide a biocide enhancement in the context of the present invention, as shown in the Examples section hereafter.

The Applicant also surprisingly found that dialcohol-comprising primary alkanolamines do not provide a biocide enhancement in the context of the present invention, as shown in the Examples section hereafter.

More recently WO 2008/088632 describes compositions useful in metalworking fluids comprising a biocidal agent and a monoalcohol primary alkanolamine with at least 6 carbons atoms. Whereas this document indicates, on page 12, that such compositions may, among a number of other applications, be applied in the environment of "mineral slurries", no further information regarding any characteristics of such mineral slurries is provided, nor is this embodiment ever exemplified.

Indeed, quite by surprise, and as shown in the examples section hereafter, the mandatory presence of ground natural calcium carbonate and/or precipitated calcium carbonate and/or dolomite and/or surface-reacted calcium carbonate in the mineral suspension is critical in order to observe a biocide enhancement in the context of the present invention.

A first aspect of the present application resides in a process for stabilising an aqueous mineral preparation comprising a step of:
(a) adding at least one aldehyde-containing and/or aldehyde-releasing and/or phenolic and/or isothiazoline biocide to said aqueous mineral preparation;
characterised in that:
said mineral comprises at least one of: a ground natural calcium carbonate, a precipitated calcium carbonate, a dolomite, a surface-modified calcium carbonate, or a mixture thereof;
said process comprises a step (b), which may be simultaneous and/or distinct relative to step (a), of adding at least one monoalcohol primary alkanol amine to said aqueous mineral preparation;
said biocide(s) are added to said aqueous preparation in an amount corresponding to from 90 to 1350 ppm based on the weight of the aqueous phase of said aqueous preparation; and
said monoalcohol primary alkanol amine(s) are added to said aqueous preparation in an amount corresponding to from 600 to 1200 ppm based on the weight of the aqueous phase of said aqueous preparation.

A second aspect of the present invention resides in the use of at least one monoalcohol primary alkanol amine as a biocidal activity enhancing compound in an aqueous ground natural calcium carbonate and/or precipitated calcium carbonate and/or dolomite and/or surface-reacted calcium carbonate-comprising mineral preparation comprising at least one aldehyde-containing and/or aldehyde-releasing and/or phenolic and/or isothiazoline biocide, where the total amount of said biocide(s) in the aqueous preparation is from 90 ppm to 1350 ppm, calculated relative to the weight of the aqueous phase of said preparation, and the total amount of said monoalcohol primary alkanol amine(s) in the aqueous preparation is from 600 to 1200 ppm, calculated relative to the weight of the aqueous phase of said preparation.

Biocides

According to a preferred embodiment of the inventive process or use, said aldehyde-containing and/or aldehyde-releasing and/or phenolic and/or isothiazoline biocide(s) are added to the aqueous preparation in a total amount of from 100 ppm to 1000 ppm, preferably in amount of from 150 ppm to 800 ppm, calculated relative to the water in the preparation.

In one embodiment of the present invention, said biocide(s) are in an undiluted, i.e. concentrated form. In another embodiment, the biocide(s) are diluted to a suitable concentration before being added to the aqueous preparation. In the diluted form, the biocide(s) are preferably dissolved in water, wherein the corresponding diluted composition comprises preferably up to 99 wt.-% of biocide, based on the total weight of the composition. More preferably, the composition in water comprises 50 to 95 wt.-% of biocide and most preferably 60 to 90 wt.-% of biocide, based on the total weight of the composition, whereby the composition may further comprise suitable stabilizers.

The aldehyde-based biocide of the present invention is preferably selected from the group consisting of formaldehyde, acetaldehyde, glyoxal, succinaldehyde, glutaraldehyde, 2-propenal, phthalic dialdehyde and mixtures thereof, and preferably is formaldehyde, glutaraldehyde and mixtures thereof.

In this application glutaraldehyde and glutardialdehyde are identical. Both names are widely used in the industry.

Preferred aldehyde-releasing biocides according to the present invention include formaldehyde-releasing biocides, acetaldehyde-releasing biocides, succinaldehyde-releasing biocides, 2-propenal-releasing biocides and mixtures thereof.

According to another embodiment, the aldehyde-releasing compound is selected from the group consisting of benzyl alcoholmono(poly)-hemiformal, ethyleneglycolhemiformal (EGHF), [1,2-Ethanediylbis(oxy)]-bis-methanol, tetrahydro-1,3,4,6-tetrakis(hydroxymethyl)imidazo[4,5-d]imidazole-2,5(1H,3H)-dione (also commonly referred to as TetraMethylolAcetyleneDiurea TMAD) and mixtures thereof.

Other preferred compounds are those having activated halogen atoms and liberating formaldehyde.

A preferred phenolic biocide is orthophenylphenol (OPP).

A preferred isothiazoline biocide is 2-methyl-4-isothiazoline-3-one (MIT), 5-chloro-2-methyl-2H-isothiazolin-3-one (CIT), 1,2-benzisothiazoline-3-one (BIT), or mixtures thereof.

According to another preferred embodiment of the present invention, the aldehyde-releasing and/or aldehyde-based biocide is used together with biocides selected from the group consisting of 5-chloro-2-methyl-2H-isothiazolin-3-one (CIT), 2-methyl-2H-isothiazolin-3-one (MIT) and mixtures thereof.

The mixtures of biocides which may be used according to the present invention are preferably dissolved in water.

An especially preferred biocide mixture comprises glutaraldehyde, 5-chloro-2-methyl-2H-isothiazolin-3-one (CIT) and 2-methyl-2H-isothiazolin-3-one (MIT).

Another especially preferred biocide mixture comprises ethyleneglycolhemiformal, 5-chloro-2-methyl-2H-isothiazolin-3-one (CIT) and 2-methyl-2H-isothiazolin-3-one (MIT).

Solids of the Aqueous Mineral Preparation

The water-insoluble solids of the aqueous mineral preparation comprise at least one of: a ground natural calcium carbonate, a precipitated calcium carbonate, a dolomite, a surface-reacted calcium carbonate, or a mixture thereof;

"Ground natural calcium carbonate" (GNCC) in the meaning of the present invention is a calcium carbonate obtained from natural sources, such as limestone, marble or chalk, and processed through a treatment such as grinding, screening and/or fractionising by wet and/or dry, for example by a cyclone or classifier.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water. PCC may be metastable vaterite, stable calcite or aragonite.

Said GNCC or PCC may be surface reacted to form a surface-reacted calcium carbonate, which are materials comprising GNCC and/or PCC and an insoluble, at least partially crystalline, non-carbonate calcium salt extending from the surface of at least part of the calcium carbonate. Such surface-reacted products may, for example, be prepared according to WO 00/39222, WO 2004/083316, WO 2005/121257, WO 2009/074492, unpublished European patent application with filing number 09162727.3, and unpublished European patent application with filing number 09162738.0.

Said GNCC or PCC may additionally be surface treated, for example with fatty acids such as stearic acid and corresponding calcium salts.

As shown in the examples section hereafter, it was surprisingly found that when the process of the invention is implemented on kaolin, the advantageous results observed using the selected minerals of the inventive process are not reproduced.

Said mineral may, however, in addition to ground natural calcium carbonate and/or precipitated calcium carbonate and/or dolomite and/or surface-reacted calcium carbonate, further comprise kaolin, kaolinitic clay, calcined kaolinitic clay, talc, calcium sulfate, quartz, attapulgite, montmorillonite, diatomaceous earth, finely divided silica, aluminium oxide, aluminium hydroxide, silicates such as aluminium silicate, pumice, sepiolite, or mixtures thereof. In such a case, said ground natural calcium carbonate and/or precipitated calcium carbonate and/or dolomite and/or surface-reacted calcium carbonate is preferably present in an amount of greater than or equal to 50% by weight, preferably greater than or equal to 60% by weight, more preferably greater than or equal to 70% by weight, even more preferably greater than or equal to 80% by weight, and even more preferably greater than or equal to 90% by weight, relative to the total weight of the mineral solids.

Clay refers to crystalline small particles of mainly hydrous silicates of aluminium, sometimes with magnesium and/or iron substitution for all or a part of the aluminium. The main groups of clay minerals are: kaolinite, the main constituent of kaolin; halloysite; illite; montmorillonite and vermiculite. The term "kaolinitic clay" used herein refers to a soft white clay that is composed mainly of the mineral kaolinite.

Kaolin is especially used in the paper industry, which uses it to coat and fill papers and boards and improves some of the optical properties of the final product, such as gloss, opacity or brightness. However, kaolin based products include paints, agricultural compositions, fibre glass products, polymer and rubber compositions, ceramic applications, catalyst supports, pharmaceuticals, cosmetics, adhesives, filter aids, and many more.

More preferably, said mineral consists essentially of only ground natural calcium carbonate, precipitated calcium carbonate, dolomite, surface-reacted calcium carbonate or mixture thereof, and most preferably consists essentially only of ground natural calcium carbonate.

Minerals having a positive surface charge at a pH of between 8 and 10 may be particularly advantageous according to the present invention.

In a preferred embodiment, the aqueous mineral preparation has a solids content of from 40 to 82% by weight, as measured according to the measurement method provided in the Examples section hereafter. More preferably, the solids content is from 50 to 80% by weight, and even more preferably from 60 to 80% by weight.

The water-insoluble solid in the preparation may have a particle size distribution as conventionally employed for the material(s) involved in the type of product to be produced. In general, 90% of the particles will have an esd (equivalent spherical diameter as measured by the well known technique of sedimentation using Sedigraph 5100 series, Micrometrics) of less than 5 µm. Coarse minerals, filler or pigment materials may have a particle esd generally (i.e., at least 90 wt.-%) in the range of 1 to 5 µm. Fine minerals materials may have a particle esd generally less than 2 µm, e.g. 50 to 99 wt.-% less than 2 µm and preferably 60 to 90 wt.-% less than 2 µm. It is preferred that the solid particles in the preparation have a $d_{50}$ value of from 0.1 to 5 µm, preferably from 0.2 to 2 µm and most preferably from 0.35 to 1 µm, for example 0.7 µm as measured using a Sedigraph™ 5100 of Micromeritics Instrument Corporation. The method and the instrument are known to the skilled person and are commonly used to determine grain size of fillers. The measurement is carried out in an aqueous solution of 0.1 wt.-% $Na_4P_2O_7$. The samples are dispersed using a high speed stirrer and supersonics.

For keeping mineral particles in such an aqueous preparation and thus ensuring that the viscosity of the preparation remains substantially the same over time, additives such as dispersing agents, thickeners or anti-settling agents are used. A suitable dispersing agent according to the present invention is preferably made of monomers and/or co-monomers selected from the group consisting of acrylic acid, methacrylic acid, itaconic acid, crotonic acid, fumaric acid, maleic anhydride acid, isocrotonic acid, aconitic acid (cis or trans), mesaconic acid, sinapinic acid, undecylenic acid, angelic acid, canellic acid, hydroxyacrylic acid, acrolein, acrylamide, acrylonitrile, dimethylaminoethyl methacrylate, vinylpyrrolidone, vinylcaprolactam, ethylene, propylene, isobutylene, diisobutylene, vinyl acetate, styrene, α-methyl styrene, methyl vinyl ketone, the esters of acrylic and methacrylic acids and mixtures thereof, wherein poly(acrylic acid) and/or poly(methacrylic acid) are preferred as dispersing agent. The skilled man will know how to correctly dose such dispersants to reach an optimal resting and process dispersion viscosity.

pH of the Aqueous Mineral Preparation

According to a preferred embodiment of the process or the use of the present invention, said aqueous mineral preparation has a pH of between 8 and 10 prior to the addition of any biocide and/or monoalcohol primary alkanol amine.

In such a case, the biocides implemented according to the present invention are preferably stable, i.e. not degraded, at a pH of between 8 and 10, at least for a time sufficient to function as a biocide when in combination with the monoalcohol primary alkanol amine.

Monoalcohol Primary Alkanol Amine

The monoalcohol primary alkanol amines employed in the present invention are preferably selected from methanolamine, ethanolamines, propanolamines, butanolamines, pentanolamines, and mixtures thereof, and preferably is 2-amino-2-methyl-1-propanol and/or 2-aminoethanol.

The ratios of said biocide(s) to monoalcohol primary alkanol amine may vary over a wide range.

The concentrations of the biocide(s) and monoalcohol primary alkanol amine(s) to be used in the aqueous preparation depend on the nature and the occurrence of the microorganisms to be controlled, the initial microbial load, and on the expected storage time of the aqueous preparations of minerals, fillers or pigments to be protected. The optimum amount to be employed within the defined ranges can be determined by preliminary tests and test series on a laboratory scale and by supplementary operational tests.

In the case where said biocide is an aldehyde-based biocide, such as glutaraldehyde, it is preferred to add said monoalcohol primary alkanol amine in an amount such that the weight ratio biocide:monoalcohol primary alkanol amine is from 1:4 to 1:1.

In the case where said biocide is a phenolic biocide, such as OPP, it is preferred to add said monoalcohol primary alkanol amine in an amount such that the weight ratio biocide:monoalcohol primary alkanol amine is from 1:4 to 1:2.

Order of Addition

According to one preferred embodiment of the inventive process, said biocide(s) and said monoalcohol primary alkanol amine are added separately to the aqueous preparation.

According to another preferred embodiment of the inventive process, said monoalcohol primary alkanol amine is added before all or part of said biocide(s). In the alternative, it may especially be preferred according to the inventive process that said biocide(s) are added before all or part of said monoalcohol primary alkanol amine.

It is especially preferred to add all of said monoalcohol primary alkanol amine before any of said biocide(s).

According to another preferred embodiment of the inventive process, said biocide(s) and said monoalcohol primary alkanol amine are added simultaneously. In this embodiment, it is possible that all or part of said biocide(s) are mixed with all or part of said monoalcohol primary alkanol amine before addition to the aqueous preparation.

Furthermore, said biocide(s) and/or the monoalcohol primary alkanol amine can be added once, e.g. before, during or after the manufacture of the preparation, or several times e.g. in specific time intervals.

Targeted Bacteria

According to the present invention, it is especially preferred that prior to addition of any of said monoalcohol primary alkanol amine or said biocide, said aqueous preparation contains bacteria selected from the group consisting of *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. and mixtures thereof, and more preferably contains bacteria selected from the group consisting of *Pseudomonas putida, Pseudomonas mendocina, Pseudomonas fluorescens, Pseudomonas alcaligenes, Pseudomonas pseudoalcaligenes, Pseudomonas entomophila, Pseudomonas syringae, Methylobacterium extorquens, Methylobacterium radiotolerants, Methylobacterium dichloromethanicum, Methylobacterium organophilu, Hyphomicrobium zavarzini* and mixtures thereof.

In one embodiment, the aqueous preparation may further or alternatively contain strains of the above bacteria which are resistant to, tolerant to and/or degrade said biocides in absence of said monoalcohol primary alkanol amine.

In the embodiment where the aqueous preparation comprises strains of the above bacteria which are resistant to, tolerant to and/or degrade said biocides in absence of said monoalcohol primary alkanol amine(s), said monoalcohol primary alkanol amine(s) in the aqueous preparation is preferably employed in an amount of from 700 to 1200 ppm, calculated relative to the weight of the aqueous phase of said preparation In the meaning of the present invention, bacteria which are "resistant" refer to bacteria having the ability to withstand the effects of said biocides when these are dosed in a total amount of from 90 to 1350 ppm, calculated relative to the amount of water in the preparation. Such resistance evolves naturally via natural selection acting upon random mutation, but it can also be engineered by applying an evolutionary stress on a population.

In the meaning of the present invention, bacteria which are "tolerant" refer to bacteria having the ability to survive in the presence of said biocides without evolving a random mutation.

Bacteria which "degrade" said biocides in the meaning of the present invention correspond to bacteria having the ability to convert said biocides into inactive forms and/or smaller molecules, e.g. by utilizing these substrates as intermediates in their pathways.

Preferably, the inventive process and use provide biocidal activity (stabilization, preservation and/or control of the microbial contamination) of aqueous preparations for a time period of at least 2 days, more preferably for at least 4 days, still more preferably for at least 6 days and most preferably for a minimum of 8 days.

Applications

According to the present invention, resulting aqueous preparations may be used in many applications, for example, in the field of paper making, paints, detergents and cosmetics.

The following examples may additionally illustrate the invention, but are not meant to restrict the invention to the exemplified embodiments.

EXAMPLES

In all of the following examples, the particle size distribution characteristics are measured using a Sedigraph™ 5100 of Micromeritics Instrument Corporation. The method and the instrument are known to the skilled person and are commonly used to determine grain size of fillers and pigments. The measurement is carried out in an aqueous solution of 0.1 wt % $Na_4P_2O_7$. The samples are dispersed using a high speed stirrer and supersonics.

All BET specific surface area measurements, quoted in $m^2/g$, are measured according to ISO 4652.

All Brookfield-viscosities are measured with a Brookfield DV-II Viscometer equipped with a LV-3 spindle at a speed of 100 rpm and room temperature (20±3° C.).

All mineral preparation solids content were measured using a Mettler Toledo MJ33 Moisture Analyser.

All biocide and lithium amounts quoted in ppm represent mg values of active content per kilogram of water in the aqueous preparation.

All quoted bacterial counts (Total Viable Count (TVC) values are in cfu/ml) in the Tables herebelow are determined after 5 days following plate-out and in accordance with counting method described in "Bestimmung von aeroben mesophilen Keimen", Schweizerisches Lebensmittelbuch, chapter 56, section 7.01, edition of 1985, revised version of 1988.

Example 1

Preparation of Slurries

Ground Natural Calcium Carbonate Slurry 1 (GNCCS1)

Ground natural calcium carbonate slurry 1 was prepared by wet grinding, in a recirculating, horizontal 1.4 liter attritor ball mill (Dyno-Mill™), a 76.4 wt.-% suspension of north-Norwegian marble having a starting esd (equivalent spherical diameter) of about 45 μm, in the presence of 0.6 wt.-%, based on the total weight of dry calcium carbonate, of a radically polymerized polyacrylic acid (MW 6000 g/Mol, polydispersity 2.6 determined by gel permeation chromatography), wherein 50 mole-% of the carboxylic acid groups are neutralized by sodium and the remaining 50 mole-% of the carboxylic acid groups are neutralized by magnesium. Following grinding, the calcium carbonate in suspension had the following particle size distribution:

| Diameter (μm) | wt.-% |
|---|---|
| <2 | 91.5 |
| <1 | 62.2 |
| <0.2 | 17.9 |

The Brookfield-viscosity of the slurry was determined as 180 mPa·s and the pH as 9.

Precipitated Calcium Carbonate Slurry 1 (PCCS1)

PCCS1 is a slurry of fine scalenohedral calcitic precipitated calcium carbonate having a 36% by weight solids content, commercialized by Omya under the trade name Omya Syncarb F3974-GO.

The pH of PCCS1 is adjusted to a pH of 9.5 by bubbling carbon dioxide gas through the slurry.

Kaolin Slurry 1 (KS1)

KS1 is a slurry of kaolin clay having a 73% by weight solids content and a pH of approximately 8, commercialized by Omya under the trade name Hydragloss 90 EM.

The slurry samples were then inoculated with 1 ml of a mixture of *Pseudomonas* species containing predominantly *Pseudomonas putida* and *Pseudomonas stutzeri*. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

TABLE 1

| Test | Invention (IN) Comparison (CO) | Slurry | BM1 (ppm on aqueous phase) | AMP (ppm on aqueous phase) | TVC (cfu/ml) |
|---|---|---|---|---|---|
| 1 | CO | GNCCS1 | — | — | $1 \times 10^6$ |
| 2 | CO | GNCCS1 | — | 750 | $1 \times 10^6$ |
| 3 | CO | GNCCS1 | 549 | — | $1 \times 10^6$ |
| 4 | CO | GNCCS1 | 1 350 | — | $1 \times 10^2$ |
| 5 | IN | GNCCS1 | 549 | 600 | $1 \times 10^2$ |
| 6 | IN | GNCCS1 | 366 | 600 | $1 \times 10^2$ |
| 7 | IN | GNCCS1 | 243 | 600 | $1 \times 10^2$ |
| 8 | IN | GNCCS1 | 450 | 750 | $1 \times 10^2$ |
| 9 | IN | GNCCS1 | 300 | 750 | $1 \times 10^2$ |
| 10 | IN | GNCCS1 | 201 | 750 | $1 \times 10^2$ |
| 11 | IN | GNCCS1 | 132 | 750 | $1 \times 10^2$ |

In parallel, the minimum inhibition concentration (MIC), that is to say the lowest concentration needed to reduce the TVC to the order of $10^2$ cfu/ml, of BM1 in the same slurry was determined to be 1350 ppm based on the weight of the aqueous phase.

The results of the above table confirm that AMP enhances the biocide function of BM1, allowing BM1 to be employed in quantities far below its MIC. Further increasing the amount of AMP allowed the amount of BM1 to be reduced even further relative to its MIC.

A comparison was then made replacing AMP with two monoalcohol tertiary aminoalcohols, dimethylethanolamine (DMEA) and diethylethanolamine (DEEA), according to Table 2, which repeats some of the results above for comparison.

TABLE 2

| Test | Invention (IN) Comparison (CO) | Slurry | BM1 (ppm on aqueous phase) | AMP (ppm on aqueous phase) | DMEA (ppm on aqueous phase) | DEEA (ppm on aqueous phase) | TVC (cfu/ml) |
|---|---|---|---|---|---|---|---|
| 1 | CO | GNCCS1 | — | — | — | — | $1 \times 10^6$ |
| 12 | CO | GNCCS1 | 549 | — | 600 | — | $1 \times 10^6$ |
| 13 | CO | GNCCS1 | 549 | — | — | 600 | $1 \times 10^6$ |
| 5 | IN | GNCCS1 | 549 | 600 | — | — | $1 \times 10^2$ |

Example 2

Biocidal Activity in Slurry

Aldehyde-Based Biocide and Isothiazoline Biocide Mixture (BM1)

Biocide mixture 1 (BM1) is an aqueous solution containing 24% by weight of GDA and 1.5% by weight of a combination of CIT and MIT (in a weight ratio CIT:MIT of 3:1), relative to the total solution weight. BM1 and AMP were introduced into 50 g samples of each of the slurries indicated in Table 1 in the listed amounts (quoted in ppm based on the weight of the aqueous phase in the slurry). References were prepared according to the same protocol but in absence of AMP and in absence of AMP and BM1.

The above results clearly demonstrate that only the biocide enhancer according to the invention provides the necessary enhancement.

Aldehyde-Based Biocide and Isothiazoline Biocide Mixture (BM1)

BM1 and AMP were introduced into 50 g samples of each of the slurries indicated in Table 3 in the listed amounts (quoted in ppm based on the weight of the aqueous phase in the slurry). References were prepared according to the same protocol but in absence of AMP and in absence of AMP and BM1.

The slurry samples were then inoculated with 1 ml of a mixture of *Pseudomonas* species containing predominantly *Pseudomonas putida* and *Pseudomonas stutzeri* that are resistant to BM1. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

TABLE 3

| Test | Invention (IN) Comparison (CO) | Slurry | BM1 (ppm on aqueous phase) | AMP (ppm on aqueous phase) | TVC (cfu/ml) |
|---|---|---|---|---|---|
| 14 | CO | GNCCS1 | — | — | $1 \times 10^6$ |
| 15 | CO | GNCCS1 | 1 350 | — | $1 \times 10^6$ |
| 16 | CO | KS1 | 450 | 750 | $1 \times 10^6$ |
| 17 | IN | PCCS1 | 450 | 750 | $1 \times 10^2$ |
| 18 | IN | GNCCS1 | 450 | 750 | $1 \times 10^2$ |
| 19 | IN | GNCCS1 | 300 | 750 | $1 \times 10^2$ |
| 20 | IN | GNCCS1 | 201 | 750 | $1 \times 10^2$ |
| 21 | IN | GNCCS1 | 132 | 750 | $1 \times 10^2$ |

The results of test 15 above attest to the resistance of the employed bacteria to BM1.

To compare the performance of a dialcohol-comprising primary alkanolamines in place of the monoalcohol primary alkanolamine, a selection of the above tests were repeated implementing 2-amino-2-ethyl-1,3-propanediol (AEPD).

| Test | Invention (IN) Comparison (CO) | Slurry | BM1 (ppm on aqueous phase) | AMP (ppm on aqueous phase) | AEPD (ppm on aqueous phase) | TVC (cfu/ml) |
|---|---|---|---|---|---|---|
| 15 | CO | GNCCS1 | 1 350 | — | — | $1 \times 10^6$ |
| 22 | CO | GNCCS1 | 1 350 | — | 1 350 | $1 \times 10^5$ |
| 23 | IN | GNCCS1 | 450 | 750 | — | $1 \times 10^2$ |

The above results clearly demonstrate that only the biocide enhancer according to the invention provides the necessary enhancement.

Aldehyde-Releasing Biocide and Isothiazoline Biocide Mixture (BM2)

Biocide mixture 2 (BM2) is an aqueous solution containing 85% by weight of EGHF and 1.5% by weight of a combination of CIT and MIT (in a weight ratio CIT:MIT of 3:1), relative to the total solution weight. BM2 and AMP were introduced into 50 g samples of each of the slurries indicated in Table 4 in the listed amounts (quoted in ppm based on the weight of the aqueous phase in the slurry). A reference was prepared according to the same protocol but in absence of AMP. References were prepared according to the same protocol but in absence of AMP and in absence of AMP and BM2.

The slurry samples were then inoculated with 1 ml of a mixture of *Pseudomonas* species containing predominantly *Pseudomonas putida* and *Pseudomonas stutzeri*. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

TABLE 4

| Test | Invention (IN) Comparison (CO) | Slurry | BM2 (ppm on aqueous phase) | AMP (ppm on aqueous phase) | TVC (cfu/ml) |
|---|---|---|---|---|---|
| 24 | CO | GNCCS1 | — | — | $1 \times 10^6$ |
| 25 | CO | GNCCS1 | 351 | — | $1 \times 10^6$ |
| 26 | CO | GNCCS1 | 750 | — | $1 \times 10^2$ |
| 27 | IN | GNCCS1 | 351 | 600 | $1 \times 10^2$ |
| 28 | IN | GNCCS1 | 234 | 600 | $1 \times 10^2$ |
| 29 | IN | GNCCS1 | 156 | 600 | $1 \times 10^2$ |
| 30 | IN | GNCCS1 | 105 | 600 | $1 \times 10^2$ |
| 31 | IN | GNCCS1 | 300 | 750 | $1 \times 10^2$ |
| 32 | IN | GNCCS1 | 201 | 750 | $1 \times 10^2$ |
| 33 | IN | GNCCS1 | 132 | 750 | $1 \times 10^2$ |
| 34 | IN | GNCCS1 | 90 | 750 | $1 \times 10^2$ |

In parallel, the minimum inhibition concentration (MIC), that is to say the lowest concentration needed to reduce the TVC to the order of $10^2$ cfu/ml, of BM2 in the same slurry was determined to be 750 ppm based on the weight of the aqueous phase.

The results of the above table confirm that AMP enhances the biocide function of BM2, allowing BM2 to be employed in quantities far below its MIC. Further increasing the amount of AMP allowed the amount of BM2 to be reduced even further relative to its MIC.

Aldehyde-Releasing Biocide and Isothiazoline Biocide Mixture (BM2)

BM2 and AMP were introduced into 50 g samples of each of the slurries indicated in Table 5 in the listed amounts (quoted in ppm based on the weight of the aqueous phase in the slurry). A reference was prepared according to the same protocol but in absence of AMP. References were prepared according to the same protocol but in absence of AMP and in absence of AMP and BM2.

The slurry samples were then inoculated with 1 ml of a mixture of *Pseudomonas* species containing predominantly *Pseudomonas putida* and *Pseudomonas stutzeri* that are resistant to BM2. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

TABLE 5

| Test | Invention (IN) Comparison (CO) | Slurry | BM2 (ppm on aqueous phase) | AMP (ppm on aqueous phase) | TVC (cfu/ml) |
|---|---|---|---|---|---|
| 35 | CO | GNCCS1 | — | — | $1 \times 10^6$ |
| 36 | CO | GNCCS1 | 750 | — | $1 \times 10^6$ |
| 37 | IN | GNCCS1 | 399 | 750 | $1 \times 10^2$ |
| 38 | IN | GNCCS1 | 267 | 750 | $1 \times 10^2$ |
| 39 | IN | GNCCS1 | 177 | 750 | $1 \times 10^2$ |
| 40 | IN | GNCCS1 | 120 | 750 | $1 \times 10^2$ |

The results of test 36 above attest to the resistance of the employed bacteria to BM1.

In parallel, the minimum inhibition concentration (MIC), that is to say the lowest concentration needed to reduce the TVC to the order of $10^2$ cfu/ml, of BM2 in the same slurry was determined to be 750 ppm based on the weight of the aqueous phase.

The results of the above table confirm that AMP enhances the biocide function of BM2, allowing BM2 to be employed in quantities far below its MIC. Further increasing the amount of AMP allowed the amount of BM2 to be reduced even further relative to its MIC.

To compare the performance of a dialcohol-comprising primary alkanolamines in place of the monoalcohol primary alkanolamine, a selection of the above tests were repeated implementing 2-amino-2-ethyl-1,3-propanediol (AEPD).

TABLE 6

| Test | Invention (IN) Comparison (CO) | Slurry | BM2 (ppm on aqueous phase) | AMP (ppm on aqueous phase) | AEPD (ppm on aqueous phase) | TVC (cfu/ml) |
|---|---|---|---|---|---|---|
| 36 | CO | GNCCS1 | 750 | — | — | $1 \times 10^6$ |
| 41 | CO | GNCCS1 | 750 | — | 1 350 | $1 \times 10^5$ |
| 37 | IN | GNCCS1 | 399 | 750 | — | $1 \times 10^2$ |

The above results clearly demonstrate that only the biocide enhancer according to the invention provides the necessary enhancement.

Example 3

Biocidal Activity on LB Broth

A comparison was made to determine the efficiency a combination identified as effective in a ground natural calcium carbonate-comprising mineral preparation above, in Luria-Bertani nutrient broth having a pH of 7.2.

This broth is inoculated with 2% of an overnight culture of a mixture of *Pseudomonas* species containing predominantly *Pseudomonas putida* and *Pseudomonas stutzeri* that are resistant to BM2, along with the AMP and BM2 amounts listed in the table below. After 24 hours, 100 µl of a 1:10 dilution in phosphate buffered saline (PBS), were plated on plate count agar (PCA). This plate was incubated at 30° C. and analysed after 5 days.

TABLE 7

| Test | Invention (IN) Comparison (CO) | Slurry or Matrix | BM2 (ppm on aqueous phase) | AMP (ppm on aqueous phase) | TVC (cfu/ml) |
|---|---|---|---|---|---|
| 42 | CO | LB broth | 300 | 750 | $1 \times 10^6$ |
| 31 | IN | GNCCS1 | 300 | 750 | $1 \times 10^2$ |

The above table shows that the results obtained on LB-nutrient broth plates are not transferable to mineral slurries.

Example 4

Biocidal Activity on GNCCS1 Filtrate

A comparison was made to determine the efficiency of a combination identified as effective in a ground natural calcium carbonate-comprising mineral preparation above, in the filtrate of that same ground natural calcium carbonate-comprising mineral preparation.

GNCCS1 was filtered in two-steps to form GNCCS1 Filtrate: the slurry liquid phase was extracted by pressure filtration (Fann Instruments filter press series 300, special hardened filter paper 3.500, retention 2-5 mm, 6 bar) and then passed through a Sartorius (Dietikon, Switzerland) 0.2 mm pore size syringe filter (Minisart RC).

BM2 and AMP were introduced into a 50 g sample of the filtrate in the amounts listed in Table 8 (quoted in ppm based on the weight of the aqueous phase).

The filtrate sample was then inoculated with 1 ml of a mixture of *Pseudomonas* species containing predominantly *Pseudomonas putida* and *Pseudomonas stutzeri* that are resistant to BM2. The sample was incubated at 30° C. for 72 hours. Thereafter, a 1:10 dilution in phosphate buffered saline (PBS) was plated on plate count agar (PCA). The plate was incubated at 30° C. and analysed after 5 days.

TABLE 8

| Test | Invention (IN) Comparison (CO) | Medium or Matrix | BM2 (ppm on aqueous phase) | AMP (ppm on aqueous phase) | TVC (cfu/ml) |
|---|---|---|---|---|---|
| 43 | CO | GNCCS1 Filtrate | 300 | 750 | $1 \times 10^6$ |
| 31 | IN | GNCCS1 | 300 | 750 | $1 \times 10^2$ |

The results show that, remarkably, the biocide enhancement is not observed in absence of the GNCC solid material.

Example 5

Biocidal Activity in Slurry

Aldehyde-Based Biocide and Isothiazoline Biocide Mixture (BM1)

Biocide mixture 1 (BM1) is an aqueous solution containing 24% by weight of GDA and 1.5% by weight of a combination of CIT and MIT (in a weight ratio CIT:MIT of 3:1), relative to the total solution weight. BM1 and 2-aminoethanol (a monoethanolamine, hereafter "MEA") were introduced into 50 g samples of each of the slurries indicated in Table 9 in the listed amounts (quoted in ppm active content based on the weight of the aqueous phase in the slurry). References were prepared according to the same protocol but in absence of MEA and in absence of MEA and BM1.

The slurry samples were then inoculated with 1 ml of a mixture of *Pseudomonas* species containing predominantly *Pseudomonas putida* and *Pseudomonas stutzeri* that are resistant to BM1. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

Test 48 below represents the same slurry as Test 47, but following a second inoculation of 1 ml of a mixture of *Pseudomonas* species.

TABLE 9

| Test | Invention (IN) Comparison (CO) | Slurry | BM1 (ppm active on aqueous phase) | MEA (ppm active on aqueous phase) | TVC (cfu/ml) |
|---|---|---|---|---|---|
| 44 | CO | GNCCS1 | — | — | $>10^4$ |
| 45 | CO | GNCCS1 | — | 675 | $>10^4$ |
| 46 | CO | GNCCS1 | 1 350 | — | $>10^4$ |
| 47 | IN | GNCCS1 | 675 | 675 | $<100$ |
| 48 | IN | GNCCS1 | 675 | 675 | $<100$ |

The results of the above table confirm that MEA enhances the biocide function of BM1, allowing BM1 to be employed in quantities below its MIC.

Aldehyde-Releasing Biocide and Isothiazoline Biocide Mixture (BM2)

Biocide mixture 2 (BM2) is an aqueous solution containing 85% by weight of EGHF and 1.5% by weight of a combination of CIT and MIT (in a weight ratio CIT:MIT of 3:1), relative to the total solution weight. BM2 and MEA were introduced into 50 g samples of each of the slurries indicated in Table 10 in the listed amounts (quoted in ppm active content based on the weight of the aqueous phase in the slurry). A reference was prepared according to the same protocol but in absence of MEA. References were prepared according to the same protocol but in absence of MEA and in absence of MEA and BM2.

The slurry samples were then inoculated with 1 ml of a mixture of *Pseudomonas* species containing predominantly *Pseudomonas putida* and *Pseudomonas stutzeri* that are resistant to BM2. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

Test 53 below represents the same slurry as Test 52, but following a second inoculation of 1 ml of a mixture of *Pseudomonas* species. Test 54 below represents the same slurry as Test 52, but following two additional inoculations of each 1 ml of a mixture of *Pseudomonas* species.

TABLE 10

| Test | Invention (IN) Comparison (CO) | Slurry | BM2 (ppm active on aqueous phase) | MEA (ppm active on aqueous phase) | TVC (cfu/ml) |
| --- | --- | --- | --- | --- | --- |
| 49 | CO | GNCCS1 | — | — | >10⁴ |
| 50 | CO | GNCCS1 | — | 675 | >10⁴ |
| 51 | CO | GNCCS1 | 750 | — | >10⁴ |
| 52 | IN | GNCCS1 | 675 | 675 | <100 |
| 53 | IN | GNCCS1 | 600 | 675 | <100 |
| 54 | IN | GNCCS1 | 600 | 675 | <100 |

The results of the above table confirm that MEA enhances the biocide function of BM2, allowing BM2 to be employed in quantities below its MIC.

Orthophenylphenol (OPP)

OPP, in the form of an aqueous solution having a concentration of 45%, and MEA were introduced into 50 g samples of each of the slurries indicated in Table 11 in the listed amounts (quoted in ppm active content based on the weight of the aqueous phase in the slurry). A reference was prepared according to the same protocol but in absence of MEA. References were prepared according to the same protocol but in absence of MEA and in absence of MEA and OPP.

The slurry samples were then inoculated with 1 ml of a mixture of *Pseudomonas* species containing predominantly *Pseudomonas putida* and *Pseudomonas stutzeri* that are resistant to OPP. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

Test 59 below represents the same slurry as Test 58, but following a second inoculation of 1 ml of a mixture of *Pseudomonas* species. Test 60 below represents the same slurry as Test 58, but following two additional inoculations of each 1 ml of a mixture of *Pseudomonas* species.

TABLE 11

| Test | Invention (IN) Comparison (CO) | Slurry | OPP (ppm active on aqueous phase) | MEA (ppm active on aqueous phase) | TVC (cfu/ml) |
| --- | --- | --- | --- | --- | --- |
| 55 | CO | GNCCS1 | — | — | >10⁴ |
| 56 | CO | GNCCS1 | — | 675 | >10⁴ |
| 57 | CO | GNCCS1 | 750 | — | >10⁴ |
| 58 | IN | GNCCS1 | 375 | 675 | <100 |
| 59 | IN | GNCCS1 | 375 | 675 | <100 |
| 60 | IN | GNCCS1 | 375 | 675 | <100 |

The results of the above table confirm that MEA enhances the biocide function of OPP.

The invention claimed is:

1. A process for stabilizing an aqueous mineral preparation comprising:
   (a) adding at least one biocide to the aqueous mineral preparation, wherein the at least one biocide is an aldehyde-containing and/or aldehyde-releasing and/or phenolic and/or isothiazoline biocide; and
   (b) adding at least one monoalcohol primary alkanol amine to the aqueous mineral preparation;

wherein:
   the mineral preparation comprises at least one of a ground natural calcium carbonate, a precipitated calcium carbonate, a dolomite, a surface-modified calcium carbonate, or any mixture thereof;
   steps (a) and (b) are performed simultaneously or separately in any order;
   the at least one biocide is added to the aqueous preparation in an amount corresponding to from 90 to 1350 ppm based on the weight of the aqueous phase of the aqueous mineral preparation; and
   the at least one monoalcohol primary alkanol amine is added to the aqueous preparation in an amount corresponding to from 600 to 1200 ppm based on the weight of the aqueous phase of the aqueous mineral preparation.

2. The process according to claim 1, wherein the at least one biocide is added to the aqueous preparation in a total amount of from 100 ppm to 1000 ppm, calculated relative to the water in the preparation.

3. The process according to claim 1, wherein the at least one biocide is added to the aqueous preparation in a total amount of from 150 ppm to 800 ppm, calculated relative to the water in the preparation.

4. The process according to claim 1, wherein the at least one biocide is at least one aldehyde-based biocide selected from the group consisting of formaldehyde, acetaldehyde, glyoxal, succinaldehyde, glutaraldehyde, 2-propenal, phthalic dialdehyde, and any mixture thereof.

5. The process according to claim 1, wherein the at least one biocide is at least one aldehyde-based biocide selected from the group consisting of formaldehyde, glutaraldehyde, and any mixture thereof.

6. The process according to claim 1, wherein the at least one biocide is an aldehyde-releasing biocide selected from the group consisting of formaldehyde-releasing biocides, acetaldehyde-releasing biocides, succinaldehyde-releasing biocides, 2-propenal-releasing biocides, and any mixture thereof.

7. The process according to claim 1, wherein the at least one biocide is an aldehyde-releasing biocide selected from the group consisting of benzyl alcoholmono(poly)-hemiformal, ethyleneglycolhemiformal (EGHF), [1,2-Ethanediylbis(oxy)]-bis-methanol, tetrahydro-1,3,4,6-tetrakis(hydroxylmethyl)imidazo[4,5-d]imidazole-2,5(1H,3H)-dione (TetraMethylol AcetyleneDiurea TMAD), and any mixture thereof.

8. The process according to claim 1, wherein the at least one biocide is a phenolic biocide comprising orthophenylphenol (OPP).

9. The process according to claim 1, wherein the at least one biocide is an isothiazoline biocide selected from the group consisting of 2-methyl-4-isothiazoline-3-one (MIT), 5-chloro-2-methyl-2H-isothiazolin-3-one (CIT), 1,2-benzisothiazoline-3-one (BIT), and any mixture thereof.

10. The process according to claim 1, wherein the at least biocide is an aldehyde-releasing and/or aldehyde-based biocide that is added together with biocides selected from the group consisting of 5-chloro-2-methyl-2H-isothiazolin-3-one (CIT), 2-methyl-2H-isothiazolin-3-one (MIT), and any mixture thereof.

11. The process according to claim 1, wherein the at least one biocide comprises glutaraldehyde, 5-chloro-2-methyl-2H-isothiazolin-3-one (CIT) and 2-methyl-2H-isothiazolin-3-one (MIT).

12. The process according to claim 1, wherein the at least one biocide comprises ethyleneglycol-hemiformal, 5-chloro-2-methyl-2H-isothiazolin-3-one (CIT) and 2-methyl-2H-isothiazolin-3-one (MIT).

13. The process according to claim 1, wherein the aqueous mineral preparation further comprises one or more of kaolin, kaolinitic clay, calcined kaolinitic clay, talc, calcium sulfate, quartz, attapulgite, montmorillonite, diatomaceous earth, finely divided silica, aluminium oxide, aluminium hydroxide, a silicate, aluminium silicate, pumice and sepiolite, wherein the ground natural calcium carbonate and/or precipitated calcium carbonate and/or dolomite and/or surface-modified calcium carbonate is present in an amount of greater than or equal to 50% by weight, relative to the total weight of the mineral solids.

14. The process according to claim 1, wherein the aqueous mineral preparation further comprises one or more of kaolin, kaolinitic clay, calcined kaolinitic clay, talc, calcium sulfate, quartz, attapulgite, montmorillonite, diatomaceous earth, finely divided silica, aluminium oxide, aluminium hydroxide, a silicate, aluminium silicate, pumice and sepiolite, wherein the ground natural calcium carbonate and/or precipitated calcium carbonate and/or dolomite and/or surface-modified calcium carbonate is present in an amount of greater than or equal to 60% by weight, relative to the total weight of the mineral solids.

15. The process according to claim 1, wherein the aqueous mineral preparation further comprises one or more of kaolin, kaolinitic clay, calcined kaolinitic clay, talc, calcium sulfate, quartz, attapulgite, montmorillonite, diatomaceous earth, finely divided silica, aluminium oxide, aluminium hydroxide, a silicate, aluminium silicate, pumice and sepiolite, wherein the ground natural calcium carbonate and/or precipitated calcium carbonate and/or dolomite and/or surface-modified calcium carbonate is present in an amount of greater than or equal to 70% by weight, relative to the total weight of the mineral solids.

16. The process according to claim 1, wherein the aqueous mineral preparation further comprises one or more of kaolin, kaolinitic clay, calcined kaolinitic clay, talc, calcium sulfate, quartz, attapulgite, montmorillonite, diatomaceous earth, finely divided silica, aluminium oxide, aluminium hydroxide, a silicate, aluminium silicate, pumice and sepiolite, wherein the ground natural calcium carbonate and/or precipitated calcium carbonate and/or dolomite and/or surface-modified calcium carbonate is present in an amount of greater than or equal to 80% by weight, relative to the total weight of the mineral solids.

17. The process according to claim 1, wherein the aqueous mineral preparation further comprises one or more of kaolin, kaolinitic clay, calcined kaolinitic clay, talc, calcium sulfate, quartz, attapulgite, montmorillonite, diatomaceous earth, finely divided silica, aluminium oxide, aluminium hydroxide, a silicate, aluminium silicate, pumice and sepiolite, wherein the ground natural calcium carbonate and/or precipitated calcium carbonate and/or dolomite and/or surface-modified calcium carbonate is present in an amount of greater than or equal to 90% by weight, relative to the total weight of the mineral solids.

18. The process according to claim 1, wherein the mineral in the aqueous mineral preparation consists essentially of ground natural calcium carbonate, precipitated calcium carbonate, dolomite, surface-modified calcium carbonate, or any mixture thereof.

19. The process according to claim 1, wherein the mineral in the aqueous mineral preparation consists essentially of ground natural calcium carbonate.

20. The process according to claim 1, wherein the aqueous mineral preparation has a solids content of from 40 to 82% by weight.

21. The process according to claim 1, wherein the aqueous mineral preparation has a solids content of from 50 to 80% by weight.

22. The process according to claim 1, wherein the aqueous mineral preparation has a solids content of from 60 to 80% by weight.

23. The process according to claim 1, wherein the aqueous mineral preparation has a pH of between 8 and 10, prior to the addition of the at least one biocide and/or monoalcohol primary alkanol amine.

24. The process according to claim 1, wherein the aqueous mineral preparation is dispersed with a dispersing agent prior to steps (a) and (b), wherein the dispersing agent made of monomers and/or co-monomers selected from the group consisting of acrylic acid, methacrylic acid, itaconic acid, crotonic acid, fumaric acid, maleic anhydride acid, isocrotonic acid, aconitic acid (cis or trans), mesaconic acid, sinapinic acid, undecylenic acid, angelic acid, canellic acid, hydroxyacrylic acid, acrolein, acrylamide, acrylonitrile, dimethylaminoethyl methacrylate, vinylpyrrolidone, vinylcaprolactam, ethylene, propylene, isobutylene, diisobutylene, vinyl acetate, styrene, α-methyl styrene, methyl vinyl ketone, esters of acrylic and methacrylic acids, and mixtures thereof.

25. The process according to claim 1, wherein the aqueous mineral preparation is dispersed with a dispersing agent prior to steps (a) and (b), wherein the dispersing agent comprises a poly(acrylic acid) and/or poly(methacrylic acid).

26. The process according to claim 1, wherein the at least one monoalcohol primary alkanol amine is methanolamine, an ethanolamine, a propanolamine, a butanolamine, a pentanolamine, or any mixture thereof.

27. The process according to claim 1, wherein the at least one monoalcohol primary alkanol amine is 2-amino-2-methyl-1-propanol and/or 2-aminoethanol.

28. The process according to claim 1, wherein the at least one biocide is an aldehyde-based biocide, and wherein the monoalcohol primary alkanol amine is added in an amount such that the weight ratio biocide:monoalcohol primary alkanol amine is from 1:4 to 1:1.

29. The process according to claim 1, wherein the at least one biocide is a phenolic biocide, and wherein the monoalcohol primary alkanol amine is added in an amount such that the weight ratio biocide:monoalcohol primary alkanol amine is from 1:4 to 1:2.

30. The process according to claim 1, wherein the at least one biocide and the at least one monoalcohol primary alkanol amine are added separately to the aqueous preparation.

31. The process according to claim 1, wherein all of the at least one monoalcohol primary alkanol amine is added before the at least one biocide.

32. The process according to claim 1, wherein the aqueous preparation prior to steps (a) and (b) comprises bacteria selected from the group consisting of *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp., and any mixture thereof.

33. The process according to claim 1, wherein the aqueous preparation prior to steps (a) and (b) comprises bacteria selected from the group consisting of *Pseudomonas putida, Pseudomonas mendocina, Pseudomonas fluorescens, Pseudomonas alcaligenes, Pseudomonas pseudoalcaligenes, Pseudomonas entomophila, Pseudomonas syringae, Methylobacterium extorquens, Methylobacterium radiotolerants, Methylobacterium dichloromethanicum, Methylobacterium organophilu, Hyphomicrobium zavarzini*, and any mixture thereof.

34. The process according to claim 1, wherein the aqueous preparation prior to steps (a) and (b) comprises bacteria that are resistant to, tolerant to and/or degrade the at least one biocide in absence of the at least one monoalcohol primary alkanol amine.

\* \* \* \* \*